(12) United States Patent
Sanderson et al.

(10) Patent No.: US 6,512,113 B1
(45) Date of Patent: Jan. 28, 2003

(54) SYNTHESIS FOR 4,10-DINITRO-2,6,8,12-TETRAOXA-4,10-DIAZATETRACYCLO [5.5.0.0$^{5,9}$0$^{3,11}$]-DODECANE

(75) Inventors: Andrew J. Sanderson, North Ogden, UT (US); Robert M. Hajik, Willard, UT (US); Thomas K. Highsmith, Ogden, UT (US); Harold E. Johnston, Brigham City, UT (US)

(73) Assignee: Alliant Techsystems Inc., Edina, MN (US)

( * ) Notice: Subject to any disclaimer, the term of this patent is extended or adjusted under 35 U.S.C. 154(b) by 51 days.

(21) Appl. No.: 09/589,113

(22) Filed: Jun. 8, 2000

Related U.S. Application Data

(60) Provisional application No. 60/138,539, filed on Jun. 10, 1999.

(51) Int. Cl.$^7$ .................... C06B 25/34; C07D 267/02
(52) U.S. Cl. ........................... 540/546; 149/92
(58) Field of Search ............... 540/546; 149/92

(56) References Cited

U.S. PATENT DOCUMENTS

| | | | |
|---|---|---|---|
| 3,111,522 A | 11/1963 | Vail et al. | 260/268 |
| 3,365,454 A | 1/1968 | Ferguson et al. | 260/268 |
| 3,369,020 A | 2/1968 | Ferguson et al. | 260/268 |
| 3,579,536 A | 5/1971 | Vail et al. | 260/326.3 |
| 5,468,313 A | 11/1995 | Wallace, II et al. | 149/53 |
| 5,498,711 A | 3/1996 | Highsmith et al. | 540/546 |
| 5,529,649 A | 6/1996 | Lund et al. | 149/19.3 |
| 5,587,553 A | 12/1996 | Braithwaite et al. | 149/19.6 |
| 5,759,458 A | 6/1998 | Haaland et al. | 164/3.3 |
| 6,107,483 A | 8/2000 | Wardle et al. | 540/546 |

*Primary Examiner*—Brenda Coleman
(74) *Attorney, Agent, or Firm*—Sullivan Law Group

(57) ABSTRACT

A process for preparing 4,10-dinitro-2,6,8,12-tetraoxa-4,10-diazatetracyclo[5.5.0.0$^{5,9}$0$^{3,11}$]-dodecane involves reacting at least one hexa-substituted piperazine derivative with at least one nitrate source and optionally at least one strong acid and heating the mixture to a temperature sufficient to induce an exothermic initial stage of the between the hexa-substituted piperazine derivative and the nitrate source. The mixture is maintained at a temperature in a range of at least ambient to not more than about 80° C. during the exothermic initial stage and at least a portion of a subsequent non-exothermic intermediate stage of the reaction by cooling the mixture during at least a portion of the exothermic initial stage of the reaction so that the reaction proceeds in a controlled manner. The mixture is then cooled to a temperature sufficiently low to prevent commencement of an exothermic NO$_x$ autocatalytic stage.

20 Claims, No Drawings

SYNTHESIS FOR 4,10-DINITRO-2,6,8,12-TETRAOXA-4,10-DIAZATETRACYCLO [5.5.0.0$^{5,9}$0$^{3,11}$]-DODECANE

RELATED APPLICATIONS

Priority is claimed of provisional application No. 60/138,539 filed in the U.S. Patent & Trademark Office on Jun. 10, 1999, the complete disclosure of which is incorporated herein by reference.

BACKGROUND OF THE INVENTION

1. Field of the Invention

This invention relates to a process of making the low sensitivity, high energy density solid oxidizer 4,10-dinitro-2,6,8,12-tetraoxa-4,10-diazatetracyclo[5.5.0.0$^{5,9}$0$^{3,11}$]-dodecane, also known as "TEX". The process provides several advantages over known processes, including faster reaction times with excellent yields and product purity.

2. Description of the Related Art

A synthesis route for preparing TEX is disclosed in U.S. Pat. No. 5,498,711, the complete disclosure of which is incorporated herein by reference. According to the '711 patent, TEX is synthesized by reacting 1,4-diformyl-2,3,5,6-tetrahydroxypiperazine and derivatives thereof with a strong acid and a nitrate source at temperatures greater than ambient temperature, such as temperatures in a range of 50° C. to 70° C. The strong acid and nitrate source of preference are sulfuric acid and nitric acid, respectively. The reaction is exothermic and is allowed to continue for two to three hours. The mixture is then poured onto ice, and a solid precipitate is isolated and washed to give a mixture which contains the TEX. The reaction is shown below:

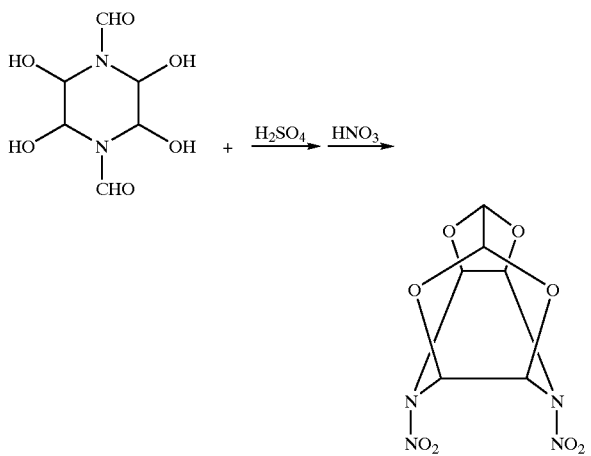

Purification can then be accomplished by heating the reaction product in nitric acid, washing with methanol, and/or washing with a base to neutralize excess acid. The pure product may be obtained by recrystallization according to standard procedures.

The synthesis route reported in the '711 patent produces TEX in yields and purities that constitute improvements over the known art. However, as is evident from the relatively long reaction times of 2 to 3 hours and the use of NO$_x$ scavengers, the '711 patent teaches not terminating the reaction until after TEX is precipitated out and NO$_x$ by-product gases are generated. The generation of NO$_x$ gases, such as NO$_2$, is an autocatalyzing reaction that becomes rapid within a relatively brief period of time, with the actual period depending on various factors, such as piperazine derivative concentration and make-up of the acid bath. Rapid generation of NO$_x$ causes fume off of reactants and product, which lowers product yield and makes the process less conducive to applications in large-scale TEX production operations.

SUMMARY OF THE INVENTION

It is, therefore, an object of this invention to address a need in the art by providing a method by which 4,10-dinitro-2,6,8,12-tetraoxa-4,10-diazatetracyclo[5.5.0.0$^{5,9}$0$^{3,11}$]-dodecane (herein referred to as TEX) can be synthesized at a sufficiently high purity and yield to permit its large scale production in an economically feasible manner.

In accordance with the objects of this invention, these and other objects are accomplished by the provision of process in which TEX is prepared by reacting at least one suitable hexa-substituted piperazine derivative (preferably 1,4-diformyl-2,3,5,6-tetrahydroxypiperazine and/or a derivative thereof) in a medium comprising at least one nitrate source and optionally at least one strong acid at temperatures equal to or greater than ambient temperature, with the reaction temperature preferably being in the range of from about 50° C. to about 80° C. During the initial stages of the reaction, which are highly exothermic, the temperature of the medium is maintained in a range of from about 50° C. to about 80° C. using cooling techniques. Subsequently, the initial exotherm ceases or substantially abates, at which point cooling can be terminated while still maintaining the reaction temperature in the range of from about 50° C. to about 80° C. Eventually, NO$_x$ generation commences via an exothermic autocatalytic reaction. Although the inventors do not wish to be bound by any theory, it is believed that the autocatalytic reaction is dependent upon there being a predetermined amount of water present in the medium. The reaction is stopped by cooling the medium to a temperature sufficiently low either to prevent onset of the NO$_x$ autocatalytic stage or, if the NO$_x$ autocatalytic stage has already commenced prior to the final cooling step, to terminate the autocatalytic generation of NO$_x$. Preferably, the autocatalytic generation of NO$_x$ is terminated before a sufficient exotherm has been released to permit the medium (while not being cooled) to be raised in temperature by more than 5° C. The reaction product is precipitated in a conventional manner, preferably by cooling at room temperature, and purified to yield TEX.

Advantageously, because the heat source is removed prior to or just after the formation of NO$_x$, the rapid release and fume off of NO$_2$ is avoided. Furthermore, unlike many conventional processes, a NO$_x$ scavenger, such as urea, may be omitted from the reaction to reduce the likelihood of by-product forming reactions. Moreover, unlike conventional processes, in a preferred embodiment the present invention is conducted in a medium which is free or substantially free of a strong acid other than nitric acid. Counter-intuitively, it has been found that the elimination of a strong acid, such as sulfuric acid, increases the TEX formation rate.

The present process can be conducted on a large manufacturing scale in which the exothermic reaction process is controllable, while directly yielding greater amounts of TEX in a high purity sufficient for use in formulating explosive compositions. These advantages are obtainable without requiring the heretofore extensive further purification or recrystallization steps.

Other objects, aspects and advantages of the invention will be apparent to those skilled in the art upon reading the specification and appended claims, which explain the principles of this invention.

DETAILED DESCRIPTION OF THE INVENTION

In the present process, TEX is prepared by addition of a predried mixture of a hexa-substituted piperazine derivative to a heated acid medium comprising at least one nitrate source and, optionally, at least one strong acid.

Hexa-substituted piperazine derivatives suitable for use in the present process are represented by the following general formula (1):

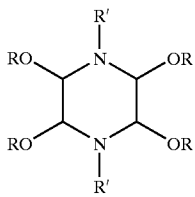

wherein —OR is a good leaving group and R is H, R", —CR"O, —COR", —COOR", —SO$_3$R", —NO, —NO$_2$, acetal (including aliphatic (e.g., formal), cycloaliphatic (e.g., cyclohexanal), and branched acetals (e.g., dimethylketal)), and cycloacetals; R' is a nitrolyzable group such as —CR"O, —COR", —SO$_2$R", —SO$_3$M, —NO$_2$, —NO, —COOR", t-butyl, cyclohexyl, and isopropyl; M is an alkali metal, preferably lithium, sodium, or potassium; R" is H, C$_1$ to C$_{10}$ alkyl, branched alkyl, cycloalkyl, and aryl (such as phenyl and substituted phenyl) and monocyclic heterocyclic moieties, and wherein each R, R', or R" can independently be the same or different. As used herein, phenyl substituents include, but are not limited to, C$_1$ to C$_{10}$ alkyl, branched alkyl, halogen, nitro, amino, substituted amino, alkoxy, acyl, and carbonyl containing moieties such as carboxyl, ester, ketone, etc. Exemplary, suitable monocyclic heterocyclic moieties contain one or more heteroatoms such as nitrogen, sulfur, and/or oxygen (e.g., triazinethiophenefuran). Representative hexa-substituted piperazine derivatives include, for example, 1,4-bis(methylsulphonyl)-2,3,5,6-tetrahydroxypiperazine, disodium-2,3,5,6-tetrahydroxypiperazine-1,4-disulphonate, 1,4-diformyl-2,3,5,6-tetraacetoxypiperazine, and, 1,4-diformyl-2,3,5,6-tetrahydroxypiperazine (THDFP). Of the above hexa-substituted piperazine derivatives, THDFP is the preferred starting material. THDFP is illustrated below by the following formula (2):

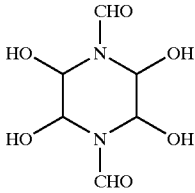

Typical hexa-substituted piperazine derivatives which may be used to synthesize TEX can be prepared by reacting glyoxal with an amide, sulfonamide, or sulfonate salt in known methods. Other hexa-substituted piperazine derivatives which may be used in the present invention are reported in Currie, A. C., et al., "Base-catalysed Reactions of Glyoxal. Part I. 1,4-Diformyl- and 1,4-Bismethylsulphonyl-Derivatives of 2,3,5,6-tetrahydroxypiperazines," *Journal of the Chemical Society* (Sect. C), pp. 491–496 (1967) and Dinwoodie, A. H. et al, "Base-catalysed Reactions of Glyoxal. Part II. 2,3,5,6-Tetrahydroxypiperazine-1,4-disulphonic Acid Derivatives," *Journal of the Chemical Society* (Sect. C), pp. 496–497 (1967).

As used herein, diacyltetraoxypiperazine derivatives also include TEX intermediate products, such as tetraoxadiazaisowurtzitane derivatives which may be prepared from diacyltetraoxypiperazine derivatives.

By preference, the present process also includes several features to reduce the amount of water present in the reaction mixture. The presence of water in the reaction mixture can affect the overall reaction by (a) increasing the NO$_x$ produced which increases reaction instability, and (b) decreasing the nitrating strength of the acid which, in turn, decreases yield of TEX.

The hexa-substituted piperazine derivative can be can be subject to a pre-drying treatment prior to addition to the acid medium to obtain, by preference, a finely ground composition. Suitable drying conditions include, for example, overnight drying or drying for about 24 hours under vacuum, typically about 10 mm Hg, at about 50° C. to about 60° C. The upper temperature is limited by the decomposition temperature of the reactants, although the upper temperature can be on the order of about 150° C. This predrying process removes residual water from these materials. As stated above, the predrying treatment results in an increased TEX yield.

The reaction vessel is optionally purged with an inert gas, and the reaction is preferably conducted in a range of from about 50° C. to about 80° C., more preferably about 50° C. to about 70° C. If the reaction is conducted at too low a temperature, for example, below about 50° C., then the formation of undesired side products is increased and yield of TEX is decreased. In contrast, too high a reaction temperature, for example, above about 80° C., results in increased reaction instability and likelihood of fume-off, increased NO$_x$ production, and lower TEX yield.

The medium to which the hexa-substituted piperazine derivative starting material is added preferably is preheated to a temperature of between about 55–60° C. Suitably the lower temperature of the medium does not fall below about 55° C. Preferably, the medium temperature is regulated to a maximum of approximately 80° C., although more preferably it is approximately 70° C.

Suitable nitronium ion sources include nitric acid and/or ammonium nitrate. Optionally, strong acids may also be used with the nitronium ion source. Representative strong acids include inorganic acids, such as sulfuric acid, oleum, nitric acid, or hydrohalo acids, such as, hydrochloric acid. Organic acids and anhydrides thereof, such as, trifluoroacetic acid (TFA), and trifluoroacetic anhydride (TFAA), are also suitable for use in the present invention. Preferably, the only strong acid present in the acid medium is nitric acid, and more preferably 100% concentration nitric acid. Where a strong acid other than nitric acid is used, the volumetric ratio of nitric acid to the combination of the other strong acids should be at least about 5:1, preferably about 10:1, and more preferably at least about 20:1. The ratio of nitrate source and strong acid (ml) to grams of hexa-substituted piperazine derivative starting material(s) preferably is at most about 8:1, and more preferably is in a range of from about 4:1 to about 5:1.

The present invention is preferably conducted in an acid medium which is free or substantially free (i.e., not more than 10 vol %) of a strong acid (other than nitric acid). Intuitively, it would seem that the rate of reaction could be increased by increasing the strong acid, e.g., sulfuric acid, concentration in the acid medium, since an increase in sulfuric acid concentration generates a corresponding increase in nitronium ion activity. However, the present inventors discovered, to their surprise, that high concentrations of strong acids, such as sulfuric acid, decrease the rate of TEX formation by promoting foaming during exothermic stages of the reaction.

An inert co-solvent may also be added to the acid medium prior to heating. The inert co-solvent acts as a thermal diluent and heat transfer agent by absorbing the heat generated by the exothermic reaction, boiling, and transferring the heat to a reflux condenser. The inert co-solvent further reduces the intensity of the exotherm and the probability of an uncontrollable reaction. Representative inert co-solvents include 1,2-dichloroethane, methylene chloride, and tetramethylene sulfone (sulfolane).

The hexa-substituted piperazine derivative can be added to the acid medium, or vice versa, at once or in a stepwise or continuous manner. The duration of each stage will depend on several factors, including reaction temperature and acid ratios. Although this invention is not thereby limited, the initial exotherm generally lasts for approximately 2–8 minutes, followed by a substantially non-exothermic stage of approximately 2–15 minutes, followed by the autocatalytic $NO_x$ stage.

The reaction product is precipitated by cooling, such as in an ice bath, followed by filtering and purifying. Currently preferred purification techniques include heating the reaction product in nitric acid, washing with methanol, and/or washing with a base to neutralize excess acid.

The pure product may be obtained by suitable separation techniques, such as crystallization or recrystallization techniques known to those skilled in the art. Typical crystallization solvents which may be used include acetonitrile, acetone, butyrolacetone, nitric acid, ethyl acetate, pyridine, DMSO, and DMF.

Typically, TEX yields are greater than 20% by weight based on the amount of piperazine starting material, and the purity is typically 98% or greater based on proton NMR analysis.

The TEX as obtained can be utilized in explosive compositions without the need for further purification or recrystallization steps. The use of TEX in explosive compositions is discussed in greater detail in U.S. Pat. No. 5,529,649, the complete disclosure of which is incorporated herein by reference. TEX may be used alone or in combination with conventional or novel solid explosive ingredients as the basis for formulating very high performance insensitive explosive compositions, such as taught in U.S. Pat. No. 5,587,553, the complete disclosure of which is incorporated herein by reference. For example, TEX may be used in combination with at least one binder, metal, and oxidizer, and optionally other explosive compounds to prepare low cost, castable explosives. Typical formulations may contain from about 5% to about 90% TEX, preferably from about 30% to about 90% TEX; from about 10% to about 30% binder; from about 0% to about 50% oxidizer; and from about 0% to about 30% reactive metal.

Representative inert polymeric binders include HTPB (hydroxy-terminated polybutadiene), PBAN (butadiene-acrylonitrile-acrylic acid terpolymer), PPG (polypropylene glycol), PEG (polyethylene glycol), polyesters, polyacrylates, polymethacrylates, CAB (cellulose acetate butyrate), or mixtures thereof. Representative energetic polymeric binders include PGN (polyglycidyl nitrate), poly-NMMO (nitratomethyl-methyloxetane), GAP (polyglycidyl azide), 9DT-NIDA (diethyleneglycol-triethyleneglycol-nitraminodiacetic acid terpolymer), poly-BAMO (poly (bisazidomethyloxetane)), poly-AMMO (poly(azidomethyl-methyloxetane)), poly-NAMMO (poly(nitraminomethyl-methyloxetane)), copoly-BAMO/NMMO, BAMO/AMMO, nitrocellulose, or mixtures thereof. The binder can optionally be halogenated, such as fluorinated ethylene propylene copolymer, chlorotrifluoroethylene and vinylidene fluoride copolymer, polyvinylidene fluoride, polydifluorochloroethylene, fluorinated polyethers, PVC, polytetrafluoroethylene, or mixtures thereof.

Representative oxidizers include AP (ammonium perchlorate), AN (ammonium nitrate), HAN (hydroxylammonium nitrate), AND (ammonium dinitramide), or mixtures thereof.

Representative reactive metals include aluminum, magnesium, boron, titanium, zirconium, or mixtures thereof.

Other explosives that can be used in combination with TEX include RDX (1,3,5-trinitro-1,3,5-triaza-cyclohexane), HMX (1,3,5,7-tetranitro-1,3,5,7-tetraaza-cyclooctane), NTO (3-nitro-1,2,4-triazol-5-one), NQ (nitroguanidine), HNIW (2,4,6,8,10,12-hexanitro-2,4,6,8,10,12-hexaazatetracyclo[$5.5.0.0^{5,9}0^{3,11}$]dodecane), TATB (1,3,5-triamino-2,4,6-trinitrobenzene), and DADNE (1,1-diamino-2,2-dinitro ethane).

TEX and a small amount of binder may also be used to prepare high solids (>90% TEX) pressable or extrudable explosives. The pressable or extrudable explosives have a high solids content and contain up to about 98.5% TEX, preferably from 50% to 98.5% TEX, and most preferably from 80% to 98.5% TEX, or a combination of TEX and other explosive. The pressable or extrudable explosives can also contain inert and/or energetic plasticizers. Representative inert plasticizers include DOA (dioctyladipate), IDP (isodecylperlargonate), DOP (dioctylphthalate), DOM (dioctylmaleate), DBP (dibutylphthalate), oleyl nitrile, or mixtures thereof. Representative energetic plasticizers include BDNPF/BDNPA (bis(2,2-dinitropropyl)acetal/bis(2, 2-dinitropropyl)formal), TMETN (trimethylolethanetrinitrate), TEGDN (triethyleneglycoldinitrate), DEGDN (diethyleneglycol-dinitrate), NG (nitroglycerine), BTTN (butanetrioltrinitrate), alkyl NENA's (nitratoethylnitramine), or mixtures thereof.

Melt cast explosives may be prepared by combining TEX with an energetic or inert material having a relatively low melt temperature (<120° C.). Representative meltable energetic materials include TNT (2,4,6-trinitrotouene) and TNAZ (1,3,3-trinitroazetidine). Other meltable energetic materials which may be used include AN/NQ eutectic or alkylammonium nitrate salts. Inert meltable materials such as polyethylene and hydrocarbon wax may also be used. The melt cast explosives may also contain a metal, oxidizer and other nitramine.

The following examples are offered to further illustrate the synthesis methods of the present invention. These examples are intended to be exemplary and should not be viewed as a limitation on the claims.

In the following examples, unless otherwise specified nitric acid (90% ACS Grade) and sulfuric acid (98%, ACS plus) from Fischer, nitric acid (100%) from Fluka, and THDFP from Parish Chemical Company were used without purification.

EXAMPLE 1

A mixture of 1000 ml of 90 vol % nitric acid (10 vol % water) and 100 ml oleum (20 wt % $SO_3$) was heated to 50° C. in a 2 liter jacketed reactor equipped with a mechanical stirrer. 228 g of THDFP were added in one lot. The solid dissolved, a colorless gas was evolved and the reaction temperature rose rapidly. Cooling was controlled (in a water bath of about 18° C.) so as to keep the temperature below 80° C. After 3.5 minutes the temperature was 78° C., the initial exotherm ceased and cooling was stopped. After 8 minutes the reaction had cooled to 64° C. but no precipitate had formed. After 8.5 minutes, the temperature rose to 65° C. and brown NOx evolution became apparent. The solution was rapidly dropped into a 12 liter jacketed reactor cooled to 0° C. The NOx evolution was quenched and a precipitate formed. The precipitate was filtered to give a white crystalline solid that was washed with water until the washings were neutral. The solid was dried and weighed. Yield 53.4 g (23.4% to weight of THDFP). Nmr analysis showed the solid to be >99% TEX.

EXAMPLE 2

50 ml of 100% nitric acid was heated to 45° C. in a 200 ml conical flask equipped with a magnetic stirrer on a water bath held at 55° C. 12.5 g of THDFP were added in one lot. The solid dissolved without foaming, a colorless gas was evolved and the temperature dropped to 40° C. Over 5 minutes the reaction temperature rose to 65° C. (while retaining in the water bath, which was maintained at 55° C.) and the acid refluxed. After 20 minutes the reaction temperature rose to 68° C., signifying the on-set of the $NO_x$ autocatalytic stage, without any precipitate apparent. The flask was then rapidly cooled to about 0° C. with ice water and a white precipitate formed. The precipitate was filtered and washed with water until the washings were neutral. The solid was dried and weighed. Yield 3.18 g (25.4% to weight of THDFP). Nmr analysis showed the solid to be >99.5 wt % TEX.

EXAMPLE 3

45 ml of 100% nitric acid and 5 ml of oleum (30 wt % $SO_3$) were mixed and heated to 45° C. in a 200 ml conical flask equipped with a magnetic stirrer on a water bath held at 55° C. 12.5 g of THDFP were added in one lot. The solid dissolved with some foaming apparent and the evolution of a colorless gas. Over 4 minutes the reaction temperature rose to 68° C. (while retaining in the water bath, which was maintained at 55° C.). After 10 minutes the reaction temperature dropped 64° C. (while retaining in the water bath, which was maintained at 55° C.). After 15 minutes the temperature rose to 68° C., signifying the on-set of the $NO_x$ autocatalytic stage, without any precipitate apparent. The flask was then rapidly cooled to about −5° C. with ice/acetone and a white precipitate formed. The precipitate was filtered and washed with water until the washings were neutral. The solid was dried and weighed. Yield 3.22 g (25.8% to weight of THDFP). Nmr analysis showed the solid to be >99.5 wt % TEX.

EXAMPLE 4–6

A mixture consisting of 1000 ml of 90 vol % nitric acid (10 vol % water) and 100 ml of oleum (30 wt % $SO_3$) was heated to about 50° C. in a 2 liter jacketed reactor equipped with a reflux condenser, a mechanical stirrer and a bottom outlet. 228 grams of THDFP were added in one lot. The temperature was monitored closely. The temperature/time profiles are shown in table 1 below. When the temperature of the reactants reached 55° C. tap water (temperature about 15° C.) was flushed through the reactor jacket to keep the reaction below 80° C. After the temperature of the reactants stopped rising the cooling was ceased and the reaction temperature was observed to continue decreasing for a short time. As soon as the temperature decrease stopped and a temperature rise of 1° C. was observed the reaction solution was drained into a 12 liter jacketed reactor that had been cooled to 0° C. to stop any further reaction. On rapid cooling a precipitate formed that was then filtered, washed and dried and found to be TEX by nmr analysis. This procedure was repeated twice (Table 1, Examples 5 and 6). In example 6, the temperature was allowed to rise to 81° C. Even though the temperature was brought down after the initial exotherm, a fume-off occurred that could not be quenched by cooling and the reactor could not be rapidlt drained into a cold tank due to the gas evolution in the boiling acid.

TABLE 1

Reaction temperature vs time for synthesis of TEX

| | Temperature (° C.) | | |
|---|---|---|---|
| Time (seconds) | Example 4 | Example 5 | Example 6 |
| 0 | 47 | 45 | 45 |
| 30 | — | 54 | 54 |
| 60 | 57 | — | 58 |
| 90 | 60 | 61 | 62 |
| 120 | 63 | 64 | 70 |
| 150 | 66 | 67 | 77 |
| 180 | 70 | 70 | 80 |
| 210 | 72 | 72 | 81 |
| 240 | 74 | 73 | 80 |
| 270 | 74 | 73 | 78 |
| 300 | 74 | 72 | 76 |
| 360 | 68 | 67 | 75 (fume off) |
| 420 | 63 | 62 | — |
| 480 | 62 | 58 | — |
| 540 | 55 | 55 | — |
| 600 | 53 | 53 | — |
| | Reaction quenched at 600s | Reaction quenched at 600s | Reaction quenched at 360s |

The foregoing detailed description of the preferred embodiments of the invention has been provided for the purpose of explaining the principles of the invention and its practical application, thereby enabling others skilled in the art to understand the invention for various embodiments and with various modifications as are suited to the particular use contemplated. The foregoing detailed description is not intended to be exhaustive or to limit the invention to the precise embodiments disclosed. Modifications and equivalents will be apparent to practitioners skilled in this art and encompassed within the spirit and scope of the appended claims.

What is claimed is:

1. A process for preparing 4,10-dinitro-2,6,8,12-tetraoxa-4,10-diazatetracyclo[$5.5.0.0^{5,9}0^{3,11}$]-dodecane by reacting at least one hexa-substituted piperazine derivative with at least one nitrate source, the reaction between the hexa-substituted piperazine and the nitrate source being characterizable by sequentially having an initial stage which is highly exothermic so that a cooling source is needed to maintain the reaction below about 80° C., an intermediate stage which is substantially non-exothermic so that the cooling source is not needed to maintain the reaction below about 80° C., and a $NO_x$ autocatalytic stage in which gases comprising $NO_x$ are generated autocatalytically and exothermically, said process comprising;
    (a) combining the hexa-substituted piperazine derivative with a medium comprising the nitrate source and optionally at least one strong acid and heating the medium to a temperature sufficient to induce the initial stage of the reaction between the hexa-substituted piperazine derivative and the nitrate source;

(b) maintaining the medium at a temperature in a range of at least ambient to not more than about 80° C. during the initial stage and at least a portion of the intermediate stage of the reaction by cooling the medium during at least a portion of the initial stage of the reaction so that the reaction proceeds in a controlled manner; and (c) cooling the medium prior to the $NO_x$ autocatalytic stage to about 0° C. to prevent commencement of the exothermic $NO_x$ autocatalytic stage.

2. The process of claim 1, wherein said hexa-substituted piperazine derivative has a structure as follows:

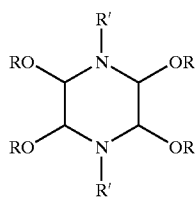

wherein —OR is a leaving group and each R is the same or different and independently selected from the group consisting of R", —CR"O, —COOR", —SO$_3$R", —NO, —NO$_2$, acetal, and cycloacetal; wherein each R' is a nitrolyzable group, each nitrolyzable group being the same or different and independently selected from the group consisting of —CR"O, —SO$_2$R", —SO$_3$M, —NO$_2$, —COOR", t-butyl, cyclohexyl, and isopropyl; wherein M is an alkali metal; wherein each R" is the same or different and independently selected from the group consisting of H, $C_1$ to $C_{10}$ alkyl, branched alkyl, cycloalkyl, phenyl, substituted phenyl, and monocyclic heterocyclic moieties.

3. The process of claim 1, wherein the medium is preheated to the temperature range of from about 50° C. to about 80° C. prior to said combining (a).

4. The process of claim 1, wherein said maintaining (b) comprises maintaining the medium at a temperature of from about 50° C. to about 70° C.

5. The process of claim 1, wherein the nitrate source is nitric acid.

6. The process of claim 5, wherein the strong acid consists of nitric acid.

7. The process of claim 6, wherein the nitric acid is at least 98 vol % concentrated.

8. The process of claim 7, wherein the nitric acid is 100% concentrated.

9. The process of claim 1, wherein the nitrate source is nitric acid and the strong acid is an acid other than nitric acid, and further wherein a volumetric ratio of the nitric acid to said strong acid is at least about 10:1.

10. The process of claim 1, wherein a ratio of the nitrate source and strong acid in millimeters to the hexa-substituted piperazine derivative is at most about 8:1.

11. A process for preparing 4,10-dinitro-2,6,8,12-tetraoxa-4,10-diazatetracyclo[5.5.0.0$^{5,9}$0$^{3,11}$]-dodecane by reacting at least one hexa-substituted piperazine derivative with at least one nitrate source, the reaction between the hexa-substituted piperazine and the nitrate source being characterizable by sequentially having an initial stage which is highly exothermic so that a cooling source is needed to maintain the reaction below about 80° C. an intermediate stage which is substantially non-exothermic so that the cooling source is not needed to maintain the reaction below about 80° C., and a $NO_x$ autocatalytic stage in which gases comprising $NO_x$ are generated autocatalytically and exothermically, said process comprising:

(a) combining the hexa-substituted piperazine derivative with a medium comprising the nitrate source and optionally at least one strong acid and heating the medium to a temperature sufficient to induce the initial stage of the reaction between the hexa-substituted piperazine derivative and the nitrate source;

(b) maintaining the medium at a temperature in a range of from at least ambient to not more than about 80° C. during the initial stage and at least a portion of the intermediate stage of the reaction by cooling the medium during at least a portion of the initial stage of the reaction so that the reaction proceeds in a controlled manner; and (c) after the exothermic $NO_x$ autocatalytic stage has commenced, cooling the medium to about 0° C. to terminate the autocatalytic generation of $NO_x$ before an exotherm is released in the $NO_x$ autocatalytic stage which raises the medium in temperature by more than 5° C.

12. The process of claim 11, wherein said hexa-substituted piperazine derivative has a structure as follows:

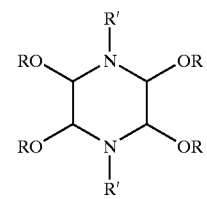

wherein —OR is a leaving group and each R is the same or different and independently selected from the group consisting of R", —CR"O, —COOR", —SO$_3$R", —NO, —NO$_2$, acetal, and cycloacetal; wherein each R' is a nitrolyzable group, each nitrolyzable group being the same or different and independently selected from the group consisting of —CR"O, —SO$_2$R", —SO$_3$M, —NO$_2$, —COOR", t-butyl, cyclohexyl, and isopropyl; wherein M is an alkali metal; wherein each R"is the same or different and independently selected from the group consisting of H, $C_1$ to $C_{10}$ alkyl, branched alkyl, cycloalkyl, phenyl, substituted phenyl, and monocyclic heterocyclic moieties.

13. The process of claim 11, wherein the medium is preheated to the temperature range of from about 50° C. to about 80° C. prior to said combining (a).

14. The process of claim 11, wherein said maintaining (b) comprises maintaining the medium at a temperature of from about 50° C. to about 70° C.

15. The process of claim 11, wherein the nitrate source is nitric acid.

16. The process of claim 15, wherein the strong acid consists of nitric acid.

17. The process of claim 16, wherein the nitric acid is at least 98 vol % concentrated.

18. The process of claim 17, wherein the nitric acid is 100% concentrated.

19. The process of claim 11, wherein the nitrate source is nitric acid and the strong acid is as acid other than nitric acid, and further wherein a volumetric ratio of the nitric acid to said strong acis is at least about 10:1.

20. The process of claim 11, wherein a ratio of the nitrate source and strong acid in millimeters to the hexa-substituted piperazine derivative is at most about 8:1.

* * * * *